United States Patent [19]

Hufford

[11] 4,093,717

[45] June 6, 1978

[54] ANTIMICROBIAL COMPOSITIONS

[75] Inventor: Charles D. Hufford, Oxford, Miss.

[73] Assignee: University of Mississippi, University, Miss.

[21] Appl. No.: 596,282

[22] Filed: Jul. 16, 1975

[51] Int. Cl.$^2$ .................. A61K 35/78; A61K 31/47
[52] U.S. Cl. .................................. 424/195; 424/258
[58] Field of Search ............................ 424/195, 258

[56] References Cited

U.S. PATENT DOCUMENTS

| 67,763 | 8/1867 | Hoeing | 424/195 |
|---|---|---|---|
| 186,141 | 1/1877 | Lipscomb | 424/195 |
| 280,281 | 6/1883 | Atkins | 424/195 |
| 440,998 | 11/1890 | Farrell | 424/195 |

OTHER PUBLICATIONS

Journal Organic Chemistry, vol. 25: pp. 1389–1390 (Aug. 1960) and vol. 26: pp. 4143–4144 (Oct. 1960).
J. Pharm. Soc. Japan, vol. 82: pp. 616–617 & 1199–1202 (1962).
J. Pharm. Soc. Japan, vol. 86: pp. 124–128 (1966).
Hufford et al, J. Pharm. Sci., vol. 64, No. 5, May 1975, pp. 789–792.

*Primary Examiner*—Donald B. Moyer
*Attorney, Agent, or Firm*—William D. Stokes

[57] ABSTRACT

Antimicrobial compositions useful in mammal. An extract of the heartwood of *Liriodendron tulipifera* L., provides components and derivatives thereof useful as antimicrobial agents; antimicrobial compositions comprising liriodenine, dehydroglaucine liriodenine methiodide and oxoglaucine methiodide compounds of and derivatives and mixtures thereof of alkaloids isolated from the extract of the heartwood of *Liriodendron tulipifera* L. The antimicrobial compositions being particularly useful against Gram positive bacteria, acid fast bacteria and fungi and yeast.

7 Claims, No Drawings

ANTIMICROBIAL COMPOSITIONS

FIELD OF THE INVENTION

The present invention is related to antimicrobial agents and more specifically to the antimicrobial activity of certain alkaloid compounds and derivatives of specific alkaloid compounds extracted from the heartwood of the tulip poplar tree, *Liriodendron tulipifera L.* More specifically, the invention is concerned with liriodenine and dehydroglaucine compounds as antimicrobial agents. Specifically, the invention relates to liriodenine methiodide and oxoglaucine methiodide derivatives of alkaloids found in the heartwood of *Liriodendron tulipifera L.* as antimicrobial agents.

BACKGROUND OF THE INVENTION

During the last few decades an intensive effort has been made to discover new, clinically useful antibiotics. Although more than a thousand antibiotics have been discovered, only a few dozen find significant clinical use. To be useful as a chemotherapeutic agent, a substance must have a low toxicity for host cells and a high toxicity for the disease causing microorganism. In other words, the antibiotic must poison the parasite and cause little or no damage to the cells of the host. It is for this reason that a substantial number of the known antibiotics are unsatisfactory as chemotherapeutic agents. In other words, they are not selective in their action on cells and thus interfere with the natural defense mechanisms. Certain disease entities remain serious problems and some of the major antibiotics have considerable drawbacks in terms of limited antimicrobial spectrum or serious side effects. These factors necessitate a continuing search for new antimicrobial agents.

SUMMARY OF THE INVENTION

The present invention provides relatively non-toxic antimicrobial compositions prepared from an extract of the heartwood of *Liriodendron tulipifera L.* which successfully overcome the disadvantages of the vast majority of the known antibiotics. In the preferred embodiments, the antimicrobial composition comprises a compound selected from the group consisting of dehydroglaucine, liriodenine, liriodenine methiodide, or oxoglaucine methiodide or mixtures thereof. The inventive compositions are admixed with a non-toxic pharmaceutically diluent carrier and may be effectively administered systemically or typically. Among the pharmaceutically acceptable carriers for oral administration are starch, dextrose, sucrose, lactose, gelatin, agar stearic and accacia, aqueous hydrochloride salt solutions or edible oils, e.g., corn or peanut oil. For topical administration any inert ointment base or cream is satisfactory such as petroleum, water soluble ointment base, hydrophilic ointment and the like. It may be appreciated that the compounds of the invention may be administered intraperitoneally, intravenously and intramuscularly in suitable pharmaceutical carriers.

DETAILED DESCRIPTION OF THE INVENTION

We discovered that an alcoholic extract of the heartwood of *L. tulipifera* exhibited an extraordinary inhibitory activity against several disease causing microorganisms such as *Staphylococcus aureus, Mycobacterium smegmatis, Candida albicans, Asperigillus niger, Bacillus subtilis,* and *Saccharomyces cerevisiae.* It was also discovered that the substituents of the alcoholic extract of the inventive composition could be divided into alkaloid and non-alkaloid fractions. It was unexpectedly discovered that the antimicrobial activity is exhibited primarily by the alkaloid fractions.

Chromatographic separation of the extracted constituents yielded four alkaloid fractions, namely glaucine, dehydroglaucine, liriodenine and michelalbine. Although it has been previously reported that oxoglaucine is a naturally occurring alkaloid of the heartwood of *L. tulipifera,* none of this compound beyond trace amounts was found in the extract. Oxoglaucine was, however, prepared by oxidation of the glaucine found.

The antimicrobial activity of the extract of the heartwood of *Liriodendron tulipifera L.*, and the four alkaloid fractions, and oxoglaucine was tested with the following organisms:

*Staphylococcus aureus* ATCC 6538
*Escherichia coli* ATCC 10536
*Mycobacterium smegmatis* ATCC 607
*Pseudomonas aeruginosa* ATCC 15442
*Candida albicans* ATCC 10231
*Saccharomyces cerevisiae* ATCC 9763
*Asperigillus niger* ATCC 16888; and
*Bacillus subtilis* ATCC 6633.

Bacterial test organisms were cultured in Eugonager and Eugonbroth (BBL), and fungi and yeasts were cultured in Mycophil (BBL) agar and broth. Antimicrobial activity was recorded as the width (in millimeters) of the clear zone of inhibition surrounding the agar well.

Of the six aforementioned compositions tested, only liriodenine and dehydroglaucine exhibited antimicrobial activity. Methiodide derivatives of liriodenine and oxoglaucine were prepared which exhibited an enhanced antimicrobial activity. The antimicrobial activity of the inventive compounds is set out in Table 2, described in detail hereinafter.

Other advantages of the antimicrobial compounds of the invention may be observed from the following examples:

EXAMPLE I 2.2 kg of air-dried, ground heartwood of *L. tulipifera* was extracted with ethanol USP by percolation at room temperature until a negative test of the percolate was observed. The solvent was removed at 40° C. under reduced pressure leaving 71 g. of residue. The residue exhibited antimicrobial activity.

35 g. of the residue was partitioned between 125 ml. each of ether and 2% citric acid. The ether layer was extracted twice more with 125 ml. of 2% citric acid, filtered to remove some interfacial solids, dried with $Na_2SO_4$, and evaporated to dryness to yield 8.6 g of residue which exhibited no antimicrobial activity. The interfacial solids weighing 5.8 g. were alkaloid negative and exhibited no antimicrobial activity.

The aqueous citric acid layers were combined, adjusted to pH 9-10 with ammonia, and extracted three times, each with 1 liter of chloroform. The aqueous layer was neutralized; a portion was evaporated to dryness and found to exhibit no antimicrobial activity. The combined chloroform layers were dried ($Na_2SO_4$) and evaporated to yield 6.2 g. of residue which exhibited antimicrobial activity.

The 6.2 g. of chloroform soluble residue was separated into tertiary phenolic and nonphenolic fractions by dissolving it in 250 ml. of chloroform and extracting three times, each with 250 ml. of 5% sodium hydroxide solution. After drying, the chloroform solution was evaporated leaving 4.7 g. of tertiary nonphenolic alkaloids which possessed all of the antimicrobial activity.

A 2 g. portion of the crude nonphenolic fraction was dissolved in chloroform and chromatographed over 200 g. of aluminum oxide (Woelm, neutral, grade III). The solvents used were: 300 ml. chloroform; 500 ml. 1% of methanol in chloroform; 300 ml. of 2% methanol in chloroform; 400 ml. of 16% methanol in chloroform; and finally the column was washed with 50% methanol in chloroform. The fractions (20 ml. each) were evaporated in tared flasks, combined according to their weights and to their similarity on TLC, and then assayed for antimicrobial activity as described in Example V below. Thin layer chromatographic analyses were carried out on Aluminum Oxide G coated plates using 4% methanol in chloroform as solvent and Dragendorff's reagent. The assay results are tabulated in Table 1 below:

Table 1

Chromatographic Separation of Tertiary Nonphenolic Fraction

| Fraction Number | Eluent | Wt. of Residue in mg | Remarks |
|---|---|---|---|
| 1-11 | CHCl$_3$ | 65 | nonalkaloidal, inactive* |
| 12-19 | CHCl$_3$; 1% CH$_3$OH—CHCl$_3$ | 400 | crystalline residue, glaucine,dehydroglaucine, active |
| 20-32 | 1% CH$_3$OH—CHCl$_3$ | 728 | amphorphus residue, inactive* |
| 33-40 | 1% CH$_3$OH—CHCl$_3$ | 118 | yellow solid, liriodenine, active |
| 41-51 | 2% CH$_3$OH—CHCl$_3$ | 206 | crystalline residue, michelalbine, inactive* |
| 52-65 | 2% CH$_3$OH—CHCl$_3$ | 84 | amphorphus residue, inactive* |
| 66-90 | 16% CH$_3$OH—CHCl$_3$ | 30 | amphorphus residue, inactive* |
| wash | 50% CH$_3$OH—CHCl$_3$ | 300 | amphorphus residue, inactive* |

*no activity was observed against any of the test organisms

EXAMPLE II

Dehydroglaucine was isolated from the Fraction 12-19 of Example I and found to exhibit all of the antimicrobial activity in that Fraction.

2.4 g. of Fraction 12-19, compiled from several columns as described in Example I, were chromatographed over 200 g. of Silica Gel G using ether as the eluent. The Silica Gel G was slurried with water first, dried at 110° C. for 12 hours, and sieved through an 80 mesh sieve before use.

The first 125 ml. of eluent contained no alkaloids, but the next 150 ml. yielded a crude alkaloid (115 mg.) which was crystallized from alcohol to yield 59 mg. of slightly colored plates (mp 113°-115° C.). Subsequent recrystallizations raised the melting point of the pale yellow plates to 121°-122° C. The mass spectrum exhibited a parent ion at m/e 353. The UV spectrum showed maxima at 260 and 332 nm while the NMR indicated a 1H singlet at δ9.60 (Ar-H) and a 3H singlet at δ3.01 (N-CH$_3$). This data is characteristic of dehydroaporphine alkaloids. Direct comparison of mp, TLC, UV and IR of this sample with a known sample of dehydroglaucine prepared by oxidizing glaucine with potassium permanganate confirmed the identity.

Melting points were determined on a Thomas-Hoover Unimelt melting point apparatus and are uncorrected. IR spectra were run in potassium bromide or chloroform using a Perkin-Elmer 257 or Beckman IR-33 infared spectrometer. NMR spectra were recorded on a JEOL C-60 HL spectrometer using deuterated chloroform as solvent and tetramethylsilane as the internal standard; chemical shifts are reported in δ (ppm) units. UV spectra were obtained in methanol on a Beckman ACTA III spectrophotometer. Mass spectral data were obtained on a DuPont-CDC 492 spectrometer.

EXAMPLE III

Liriodenine was isolated from Fraction 33-40 of Example I and contained all of the antimicrobial activity in this fraction.

Crystallization of the residue of Fraction 33-40 of Example I (118 mg.) from chloroform yielded 85 mg. of yellow needles having a mp of 280°-281° C. The mp, IR, and UV, determined in the same manner as described in Example II, were consistent with data reported for the yellow alkaloid, liriodenine, as reported by M. A. Buchanan and E. E. Dickey in J. Org. Chem, Vol. 25, p. 1389 (1960). Direct comparison of mp, mmp, IR and UV with a known sample of liriodenine confirmed the identity.

EXAMPLE IV

Liriodenine methiodide was prepared from the liriodenine isolated in accordance with Example 1. A 2.71 gm sample of liriodenine was reflexed in 30 ml of chloroform and then 10 ml of iodomethane was added. After 24 hours at reflux, the solution was cooled, excess iodomethane removed, and the red crystals filtered. Crystallization from methanol yielded 2.24 gm liriodenine methiodide, mp 235 d.

EXAMPLE V

Oxoglaucine was prepared by oxidation of glaucine. 2.4 g. of glaucine in 75 ml. of acetone was oxidized by adding a solution of 6 g. of potassium permanganate in 450 ml. of acetone dropwise over 2 hours followed by stirring for 6 hours. Then another 6 g. of potassium permanganate in 450 ml. of acetone was added and allowed to stir for 12 hours. The suspension was filtered through Celite and the clear orange solution was evaporated to dryness. Crystallization from a small volume of chloroform yielded 0.578 g. of orange needles of oxoglaucine having a mp 224°-225° C. Recrystallization yielded orange needles, mp 229°-230° C, of oxoglaucine whose identity was confirmed by comparison of the mp, mmp, TLC, and IR, obtained using the same procedure as in Example II, with those of a known sample of oxoglaucine.

EXAMPLE VI

Oxoglaucine methiodide was prepared from oxoglaucine in accordance with the process of Example V. A 31 mg sample of oxoglaucine was refluxed in 8 ml of acetone until it completely dissolved (approximately 30 minutes) and then 0.75 ml of iodomethane was added. The solution was refluxed until it became brown. The crystals were then collected by filtration to yield 15 mg of the methiodide salt, mp 255 d.

EXAMPLE VII

Qualitative evaluation of antimicrobial activity of the inventive extracts, fractions, and pure compounds was accomplished using an agar well diffusion assay. As set out hereinbefore, the inventive compositions were tested for activity against the following microorganisms: *Staphylococcus aureus* ATCC 6538; *Escherichia coli*

ATCC 10536; *Mycobacterium smegmatis* ATCC 607; *Pseudomonas aeruginosa* ATCC 15442; *Candida albicans* ATCC 10321; *Saccharomyces cerevisiae* ATCC 9763; and *Asperigillus niger* ATCC 16888. In addition, the compounds of the preferred embodiments were also tested against *Bacillus subtilis* ATCC 6633. Bacterial test organisms were cultured in Eugonagar and Eugonbroth (BBL), and fungi and yeasts were cultured in Mycophil (BBL) agar and broth.

Plates for assay were prepared by uniformly seeding sterily, partially cooled, molten agar with dilutions of test organisms grown in broth or suspensions of conidia produced on agar slants (A. niger). The seeded agar medium was dispensed into 100 × 15 mm sterile petri dishes (15 ml per dish). Cylindrical plugs were removed from the solidified agar plates, using a sterile cork borer, to produce wells having a diameter of approximately 11 mm. One hundred microliters of a solution or suspension of an extract, fraction, or pure compound was added to each well. The extracts and fractions were tested as solutions or suspensions in a concentration of 20 mg/ml; pure compounds were tested at 1 mg/ml. When solvents other than water were required to dissolve extracts or compounds, solvent blanks were run against each test organism.

Plates prepared as described above were incubated as follows: Bacteria were grown at 37° C. for 24 hours, with the exception of *M. smegmatis*, which grows more slowly and requires incubation at 37° C. for 48 hours, before reading. Fungi or yeast were incubated at 25° C. for 24 hours, before growth was evident.

Antimicrobial activity was recorded as the width (in mm) of the clear zone of inhibition surrounding the agar well. Results for those samples which exhibited antimicrobial activity are shown in Table 2.

(Calbiochem "A" grade) at the same concentrations as above were used as standard antibiotics for comparison with the activities of the alkaloids against bacteria and yeast species, respectively. Cultures used in the serial dilution assay included *S. aureus*, *B. subtilis*, *M. smegmatis*, *C. albicans*, and *S. cerevisiae*. Readings were taken after incubation times of 24 hours for all organisms except *M. smegmatis*, which was read at 72 hours. The concentration mcg/ml of the tube of highest dilution which was free from growth was recorded as the minimal inhibitory concentration in Table 3.

Table 3

| Compound | Minimum Inhibitory Concentration (mcg/ml) of Active Compounds | | | | |
|---|---|---|---|---|---|
| | S. aureus | B. Subtilis | M. Smegmatis | C. Albicans | S. cerevisiae |
| 1. liriodenine | 3.1 | 0.39 | 1.56 | 6.2 | 6.2 |
| 2. liriodenine methiodide | 6.2 | 3.1 | 3.1 | 0.78 | 3.1 |
| 3. oxoglaucine methiodide | 25 | 25 | 25 | 1.56 | 25 |
| 4. dehydroglaucine | 25 | 25 | 25 | 25 | 50 |
| 5. streptomycin* sulfate | 3.1 | 1.56 | 0.78 | — | — |
| 6. amphotocericin B* | — | — | — | 0.78 | 0.78 |

*Common antibiotics used as controls.

As may be appreciated from the data in Table 3, liriodenine and liriodenine methiodide show in vitro activity comparable to that of streptomycin sulfate and amphotericin B. Dehydroglaucine has a similar spectrum of activity to liriodenine and liriodenine methiodide but is not as potent. Oxoglaucine methiodide has a similar activity to dehydroglaucine but is particularly active against *C. albicans*.

The present invention has been described in detail with particular reference to the preferred embodiments thereof, however, it is understood that modifications may be made without departing from the spirit and scope of the invention.

We claim:

1. An antimicrobial composition comprising a compound or mixture of compounds derived from an alcoholic extract of the heartwood of *Liriodendron tulipifera* L. selected from the group consisting of liriodenine, liriodenine methiodide, dehydroglaucine, oxoglaucine methiodide and mixtures thereof in admixture with a non-toxic pharmaceutically acceptable carrier in a therapeutically effective concentration.

2. The antimicrobial composition of claim 1 wherein said antimicrobial agent is liriodenine.

TABLE 2

| Sample | Antimicrobial Activity of Extracts, Fractions, and Compounds | | | | | |
|---|---|---|---|---|---|---|
| | S. aureus | B. subtilis | M. smegmatis | C. Albicans | S. cerevisiae | A. niger |
| Alcohol extract | 4 mm | not tested | 10 mm | 2 mm | not tested | 5 mm |
| Tertiary nonphenolic fraction | 8 mm | not tested | 12 mm | 5 mm | not tested | 9 mm |
| fraction 12 – 19 | 3 mm | not tested | 2 mm | 1 mm | not tested | — |
| fraction 33 – 40 | 5 mm | not tested | 10 mm | 3 mm | not tested | 10 mm |
| liriodenine | 5 mm | 8 mm | 11 mm | 3 mm | 5 mm | 11 mm |
| liriodenine methiodide | 6 mm | 6 mm | 14 mm | 17 mm | 15 mm | 4 mm |
| dehydroglaucine | 4 mm | 7 mm | 8 mm | 6 mm | 6 mm | — |
| oxoglaucine methiodide | 9 mm | 9 mm | 10 mm | 10 mm | 11 mm | — |

EXAMPLE VIII

Quantitive assay of antimicrobial activity of the inventive compositions against selected test organisms was made using a two-fold serial dilution in Eugonbroth or Mycophil broth. The concentration of pure alkaloids in the initial dilution tube was 50 mcg/ml. Streptomycin sulfate (Nutrional Biochemical) and amphotericin B 3. The antimicrobial composition of claim 1 wherein said antimicrobial agent is liriodenine methiodide.

4. The antimicrobial composition of claim 1 wherein said antimicrobial agent is dehydroglaucine.

5. The antimicrobial composition of claim 1 wherein said antimicrobial agent is oxoglaucine methiodide.

6. The process of detoxifying Gram positive bacteria, acid fast bacteria and fungi and yeast infecting mammal which consists essentially of administering to said mammal a composition consisting of a compound or mixture of compounds derived from the residue obtained from the alcoholic extract of the heartwood of *Liriodendron tulipifera L.* selected from the group consisting of liriodenine, liriodenine methiodide, dehydroglaucine, oxoglaucine methiodide and mixtures thereof in admixture with a non-toxic pharmaceutically acceptable carrier, said compound being in a therapeutically effective concentration.

7. The process of detoxifying Gram positive bacteria, acid fast bacteria and fungi and yeast infecting mammal which consists essentially of administering to said mammal a composition consisting of a compound selected from the group consisting of liriodenine, dehydroglaucine, liriodenine methiodide and oxoglaucine methiodide in admixture with a non-toxic pharmaceutically acceptable carrier, said compound being in a therapeutically effective concentration.

* * * * *